United States Patent
Duguet et al.

(10) Patent No.: US 9,630,838 B2
(45) Date of Patent: Apr. 25, 2017

(54) FERROFLUIDS STABLE IN NEUTRAL MEDIA AND MODIFIED FERROFLUIDS MODIFIES OBTAINED BY MODIFICATION OF THE SURFACE OF THE PARTICLES OF SAID FERROFLUIDS

(75) Inventors: Etienne Duguet, Begles (FR); Stéphane Mornet, Artigues Pres Boardeaux (FR); Joseph Portier, Gradignan (FR)

(73) Assignee: CENTRE NATIONAL DE LA RECHERCHE SCIENTIFIQUE (C.N.R.S), Paris (FR)

( * ) Notice: Subject to any disclaimer, the term of this patent is extended or adjusted under 35 U.S.C. 154(b) by 2895 days.

(21) Appl. No.: 10/558,069

(22) PCT Filed: May 13, 2004

(86) PCT No.: PCT/FR2004/001169
§ 371 (c)(1),
(2), (4) Date: May 2, 2006

(87) PCT Pub. No.: WO2004/107368
PCT Pub. Date: Dec. 9, 2004

(65) Prior Publication Data
US 2007/0090323 A1  Apr. 26, 2007

(30) Foreign Application Priority Data
May 23, 2003  (FR) ..................... 03 06279

(51) Int. Cl.
*B82Y 25/00*  (2011.01)
*A61K 49/18*  (2006.01)
*B82Y 5/00*  (2011.01)
*H01F 1/00*  (2006.01)
*H01F 1/44*  (2006.01)

(52) U.S. Cl.
CPC ............ *B82Y 25/00* (2013.01); *A61K 49/186* (2013.01); *A61K 49/1848* (2013.01); *A61K 49/1863* (2013.01); *B82Y 5/00* (2013.01); *H01F 1/0054* (2013.01); *H01F 1/0063* (2013.01); *H01F 1/445* (2013.01); *Y10T 428/2982* (2015.01)

(58) Field of Classification Search
CPC ............ A61K 49/1848; A61K 49/186; A61K 49/1863; B82Y 5/00; B82Y 25/00; H01F 1/0063; H01F 1/445; H01F 1/26; C01G 51/00; B32B 15/02
USPC .................. 424/9.32, 9.322, 9.323
See application file for complete search history.

(56) References Cited

U.S. PATENT DOCUMENTS

| | | | | |
|---|---|---|---|---|
| 4,554,088 A | * | 11/1985 | Whitehead et al. | 252/62.54 |
| 4,827,945 A | * | 5/1989 | Groman et al. | 424/9.32 |
| 4,965,007 A | | 10/1990 | Yudelson | |
| 5,262,176 A | | 11/1993 | Josephson et al. | |
| 5,492,814 A | * | 2/1996 | Weissleder | 435/7.25 |
| 5,776,360 A | | 7/1998 | Sieber | |
| 6,183,658 B1 | * | 2/2001 | Lesniak et al. | 252/62.56 |
| 6,638,494 B1 | * | 10/2003 | Pilgrimm | 424/9.323 |
| 2002/0034537 A1 | * | 3/2002 | Schulze et al. | 424/450 |

FOREIGN PATENT DOCUMENTS

WO  WO 99/63079   12/1999
WO  WO 00/56288  *  9/2000  ............... A61K 9/51

OTHER PUBLICATIONS

Gao, et al., Applied Surface Science, 2005, 250, p. 273-279 (abstract).*
Esumi, Bull. Chem. Soc. Jpn., 1983, 56, p. 331-332.*

* cited by examiner

Primary Examiner — Michael G Hartley
Assistant Examiner — Leah Schlientz
(74) Attorney, Agent, or Firm — Young & Thompson

(57) ABSTRACT

The invention relates to aqueous dispersions, comprising particles based on a magnetic iron oxide with dimensions of ≤20 nm, the surface of which is modified by the grafting of aminated groups R with a covalent bonding to the surface of said particles, wherein the isoelectronic point of particles with such a modified surface is ≥10. The invention further relates to a method for production of said aqueous suspensions and a method for modification of the surface of the particles present in said dispersions, in particular, by the immobilisation of polysaccharides such as dextrans, particularly for the formulation of magnetic compositions which may be administered in vivo and in particular for the formulation of injectable compositions of contrast agents for MRI.

41 Claims, No Drawings

FERROFLUIDS STABLE IN NEUTRAL MEDIA AND MODIFIED FERROFLUIDS MODIFIES OBTAINED BY MODIFICATION OF THE SURFACE OF THE PARTICLES OF SAID FERROFLUIDS

The present invention relates to aqueous dispersions of particles of nanometric dimensions based on magnetic iron oxide, with a modified surface, which exhibit a very low degree of interparticle agglomeration, especially in a neutral medium. These dispersions of magnetic particles with a modified surface and which are essentially separate are especially useful for the preparation of compositions of diagnostic or therapeutic interest, and very specifically in the preparation of compositions suitable for administration by injection.

Various types of compositions comprising nanometric (with dimensions of less than 100 nm) magnetic particles dispersed in liquid dispersing media of aqueous nature (water or aqueous solutions) or else of organic nature (hydrocarbons, kerosene, xylene, toluene, polyglycols or phenyl ethers, in particular) are currently known.

In these compositions, the most widely used particles are particles based on iron ($\alpha$-Fe) or on cobalt ($\alpha$-Co) and particles based on magnetic iron oxide(s), such as ferrites (namely, generally, oxides of overall formula $M^{II}Fe^{III}Fe^{II}O_4$, wherein $M^{II}$ denotes a metal selected from Fe, Co, Ni, Cd, Mn, Zn or Mg in its oxidation state of +II).

Although they generally exhibit magnetic properties which are less pronounced than those of $\alpha$-Fe or $\alpha$-Co particles, particles based on magnetic iron oxides (and especially particles based on ferrites) are actually more stable with regard to oxidation and they are consequently more widely used, especially in aqueous dispersions. In this context, one makes especially use of ferrimagnetic particles based on magnetite ($Fe_3O_4$) or on maghemite ($\gamma$-$Fe_2O_3$)

Dispersions, especially aqueous dispersions, of particles based on magnetic iron oxides are often depicted by the generic term of "ferrofluid". This name comes from the fact that, when this type of dispersion exhibits a sufficiently high concentration of iron oxide particles, the application of a magnetic field gradient causes the particles to move, whereby particles carry along the liquid. At a macroscopic level, the behavior observed is schematically that of a "magnetic liquid".

One of the problems to be solved when a ferrofluid is synthesized is the stabilization of the magnetic particles with regard to agglomeration.

This is because, generally, in a ferrofluid (as in any dispersion of oxide particles of nanometric dimensions), the oxide-based particles have a tendency to be mutually attracted, especially due to attractive interactions of Van der Waals type. Therefore, it is necessary to ensure the stabilization of the dispersion, so as to inhibit the natural phenomenon of flocculation. So as to inhibit the phenomenon of interparticle agglomeration, use is generally made, in dispersions of "ferrofluid" type, of particles exhibiting surface charges inducing repulsive interactions between the particles ("electrostatic stabilization") or particles exhibiting macromolecules at their surface, which are adsorbed or grafted, ("steric stabilization"). When both stabilization methods are used in conjunction, the term used is "electrosteric stabilization".

The difficulty to stabilize a ferrofluid increases with decrease of the size of the particles present and with increase of the concentration of particles.

Now, especially so as to obtain sufficiently pronounced magnetic properties, it is generally desirable that a ferrofluid has a high concentration of particles.

Furthermore, in a dispersion of magnetic particles of "ferrofluid" type, it is particularly advantageous for the oxide particles to be small particles, preferably of less than 20 nm, and typically between 3 and 15 nm. As a matter of fact, with such particles sizes, the particles are generally monocrystalline and each of the particles is then a "monodomain" magnetic particle possessing an appropriate magnetic moment and behaving as a magnetic macrospin. The ferrofluid then exhibits an overall behavior of paramagnetic nature ("superparamagnetism" phenomenon), that is to say that the particles do not retain residual magnetism in the absence of a magnetic field. This absence of residual magnetism provides the advantage of not inducing magnetic interactions between the particles, liable to cause an agglomeration, contrary to the effect which would be observed with nonmonocrystalline magnetic particles, which tend to be attracted to one another in order to balance their residual magnetic moments.

It should also be noted that, when one desires to use dispersions of magnetic particles for administration to animals or man, for example as contrast agent for MRI, it is often necessary to have available particles exhibiting a hydrodynamic diameter which is as low as possible, in particular so as to pass through the maximum of biological membranes. When the dispersions are injected intravenously, the reduction in the size of the particles is also necessary in order to avoid phenomena of obstruction of the blood network, for example in the capillaries, especially in order to limit the risks of embolisms.

One of the commonest means for obtaining aqueous dispersions of particles of a magnetic iron oxide exhibiting a degree of interparticle agglomeration which is as small as possible consists in controlling the pH of the dispersing aqueous medium either at a value of less than 5 (acidic ferrofluid) or at a value of greater than 10 (basic ferrofluid).

On this subject, it has been observed that, in an aqueous medium, chemosorption of water molecules is observed at the surface of particles of iron oxides, such as ferrites, which chemosorption results in the formation of hydroxyl entities which can be represented diagrammatically by ≡Fe(III)—OH. These hydroxyl entities are amphoteric and, depending on the pH of the aqueous medium, they result in the formation of positive or negative charges, according to the following reaction schemes:

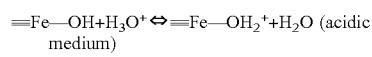
≡Fe—OH+$H_3O^+$ ⇔ ≡Fe—$OH_2^+$+$H_2O$ (acidic medium)

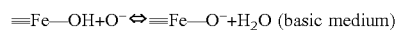
≡Fe—OH+$O^-$ ⇔ ≡Fe—$O^-$+$H_2O$ (basic medium)

However, at pH values of between 5 and 10, the density of charges present at the surface of iron oxide particles is too low to provide stabilization of electrostatic type. On this subject, it should be noted that the isoelectric point of an iron oxide, namely the pH at which the charges present at the surface of the iron oxide cancel each other out, is generally of the order of 7 (it is generally between 6 and 9 and typically has a value of 7, in particular in the case of maghemite). Thus, it turns out that the stability of an aqueous ferrofluid (in particular of USPIO type) at a pH of the order of 7 cannot be obtained by simple electrostatic stabilization. This constitutes a limitation on the use of the particles of iron oxide of ferrite type, especially for medical applications (contrast agent for MRI, in particular), wherein it is precisely necessary to provide dispersions which are stable at a physiological pH, namely at a pH of the order of 7.4.

In order to provide aqueous ferrofluids with stability at neutral pH, stabilization methods have consequently been developed, which employ grafting of molecules at the surface of the particles, for the purpose of shifting the isoelectric point of the dispersion and consequently the range of stability of this dispersion with regard to interparticle agglomeration.

The "isoelectric point" of the particles of a ferrofluid to which reference is made in the present description denotes the value of the pH of the dispersion for which the surface charge(s) carried by said particles cancel each other out. This isoelectric point (or IEP) can in particular be determined by zeta potential measurement, namely by measuring the zeta potential of a dispersion of the particles at different pH values, for example according to the method described by R. J. Hunter in *Zeta Potential in Colloid Science, Principles and Applications*, Academic Press, London (1986).

Generally, a ferrofluid is stable with regard to interparticle agglomeration in a pH range remote from the IEP, whereas, at pH values of the order of the IEP, the ferrofluid becomes unstable. The region of instability can be more or less narrow around the value of the IEP, the extent of this region varying in particular according to the size of the particles of the ferrofluid and the number of charged surface sites. Thus, in general, the extent of the region of instability decreases with the size of the particles.

In the majority of cases, a ferrofluid is stable at pH values of less than (IEP−2) (and greater than (IEP+2)). However the region of stability of the ferrofluid may vary to a greater or lesser extent. In any case, a ferrofluid loses its stability at a pH in the vicinity of the IEP. In order to obtain ferrofluids which are stable in a neutral medium, attempts have thus been made to obtain ferrofluids having an IEP which is as remote as possible from the value of 7. In this context, one has especially described ferrofluid compositions stabilized in a neutral medium, exhibiting a surface modified by aminated entities, obtained by grafting molecules, such as aminosilanes.

However, the processes developed for this purpose generally result in processes of agglomeration of the particles during grafting. For this reason, they make it possible only to obtain particle aggregates grafted at the surface. As example of process of this type, leading to the production of large particles, mention may e.g. be made,to the process described for example by Whitehead et al. in U.S. Pat. No. 4,695,393.

In order to avoid the phenomenon of interparticle aggregation during grafting by entities of aminosilane type, provision has been made to carry out the grafting reaction while subjecting the reaction medium to an ultrasound treatment for the purpose of obtaining a dispersion of the oxide particles in the medium in which the grafting is carried out. On this subject, reference may especially be made to the paper by Lesniak et al. in *Mat. Res. Soc. Symp. Proc.*, 432, 169-174,(1997). In these processes, it is recommended to carry out the ultrasound treatment under conditions which are as forceful as possible, so as to be able to obtain optimum grafting. Under these conditions, this type of process can result in the production of particles of reduced size and/or the particles can have an IEP which can reach values of the order of 9.5, which makes it possible to envisage their use up to a pH of the order of 7.5.

Now, the inventors have unexpectedly discovered that it is possible to carry out a grafting of particles based on an iron oxide resulting in the production of particles of reduced size, without needing, for this, to carry out the forceful ultrasound treatment taught by the prior art, with the proviso that the grafting is carried out on particles based on an iron oxide in the form of a stable colloidal dispersion of particles and that the surface treatment is implemented under conditions of stability of the colloidal dispersion (namely, of preventing the flocculation or the aggregation of the particles). In this context, the inventors have demonstrated that the hydrodynamic diameter of the grafted particles obtained is substantially equal (indeed even identical, generally) to the hydrodynamic diameter of the particles of the starting colloidal dispersion.

Even more surprisingly, the studies of the inventors have furthermore evidenced that a grafting carried out on particles based on iron oxide which are maintained in the form of a colloidal dispersion during the grafting makes it possible to obtain particles having a higher isoelectric point than that of the particles obtained by the processes currently known, that employ grafting under ultrasound treatment. In this connection, without wishing to be committed to any specific theory, it appears that, entirely unexpectedly, the use of a colloidal dispersion which is stable per se, rather than a dispersion of particles kept in dispersion under a ultrasound treatment, results in a more homogeneous grafting of the particles, which renders the particles obtained more stable in a neutral medium.

More unexpectedly still, the inventors have also discovered, during their studies, that the grafting of compounds, such as aminosilanes, to the oxide particles of a ferrofluid substantially improves the thermostability of the particles, this being in particular the situation in the case where the particles are maghemite particles, which can in particular prove to be advantageous for their use in the preparation of composite materials or ceramics possessing magnetic properties at high temperature.

In addition, the surface modification of the invention actually makes it possible to obtain particles grafted at the surface by aminated groups, via which chemical entities, in particular macromolecules, can be immobilized at the surface of the grafted particles. Especially, the surface modification carried out by the inventors makes possible an immobilization of molecules of polysaccharides, and in particular of dextran molecules, via the establishment of covalent bonds between the polysaccharides and the aminated groups.

In this specific context, the studies of the inventors have evidenced that, surprisingly, the grafting of macromolecules, such as polysaccharides, to aminated groups can be carried out while retaining a population of essentially separate particles and while additionally retaining a low hydrodynamic diameter, typically of less than 50 nm and generally of less than 40 nm.

This possibility of obtaining magnetic particles which (i) have a reduced hydrodynamic diameter and (ii) are grafted at the surface by covalently bonded macromolecules of polysaccharide type (e.g. dextran), is of great interest, especially in the preparation of compositions for administration to animals or man and in particular in the preparation of contrast agent compositions for magnetic resonance imaging (MRI).

As a matter of fact, the dispersions of particles thus obtained constitute a particularly advantageous alternative to the dispersions of magnetic particles currently used in particular as contrast agents for MRI in vivo.

At the present time, current dispersions of magnetic particles intended for in vivo administration are particles exhibiting a hydrodynamic diameter which is as small as possible, typically less than 100 nm (especially in order to ensure good tissue diffusion), and having a surface covered by hydrophilic macromolecules, such as dextran, generally adsorbed on the surface. This "dressing" of the surface of the particles is carried out especially in order to render the surface of the particles hydrophilic and electrically neutral, so as to slow down the detection of the particles by the immune system (that is to say, in order to increase the half life of the particles in vivo and slow down their removal, for example, in the liver).

These particles dressed with molecules of dextran type of the prior art generally have a relatively large size, especially due to the fact that the dressing with dextran is carried out under conditions generally resulting in an agglomeration of several magnetic particles, which are surrounded by a layer of dextran. However, under certain synthesis conditions, such as those described, for example, in U.S. Pat. No. 4,452,773,success is achieved in producing particles of relatively small size, typically of the order of 50 nm which are generally denoted by the term of "USPIO" (Ultrasmall SuperParamagnetic Iron Oxides) or of "MION" (Microcrystalline Iron Oxide Nanoparticles). However, whatever their size, the magnetic particles dressed with macromolecules of dextran type currently known generally result in phenomena of depletion of the dextran when they are administered in vivo, which reduces their residence time in the organisms into which they are introduced.

In contrast, the dispersions of magnetic particles grafted at the surface by macromolecules of dextran type which have been developed by the inventors do not exhibit such disadvantages, since the macromolecules of dextran type are covalently bonded to the surface of these particles, which makes it possible to avoid the phenomena of depletion observed with the abovementioned ferrofluids of "USPIO" or "MION" type.

In addition, the studies carried out by the inventors have evidenced that, in contrast to the particles of the ferrofluids of "USPIO" or "MION" type, the particles with surfaces modified by covalently bonded macromolecules of polysaccharide type which have been discovered by the inventors can themselves be functionalized, for example by molecules of biological interest (for example effector molecules for targeting to specific cells or organs, or alternatively active principles or oligonucleotides), this being the case without consequently increasing the hydrodynamic diameter of the particles and while additionally retaining, generally, a population of essentially separate particles.

On the basis of these discoveries, one aim of the present invention is especially to provide aqueous ferrofluids which exhibit a very small particle size and which are stable in a neutral medium, in particular in a physiological medium. More specifically, a very particular aim of the invention is to provide ferrofluids which are stable up to a pH of 8 and in particular stable in the pH range extending from 6 to 8.

Generally, the present invention also aims at providing a process which makes it possible to shift the region of stability of a colloidal ferrofluid into a pH range extending up to 8,encompassing the pH of physiological media, without modifying the magnetorheological properties of this ferrofluid and in particular while essentially maintaining its magnetic properties and the hydrodynamic diameter of the particles.

Another object of the invention is to provide aqueous ferrofluids having a low degree of interparticle agglomeration in a neutral medium and wherein the particles can be grafted by chemical entities, such as macromolecules, without inducing phenomena of interparticle aggregation. In this context, the invention more aims at providing ferrofluids comprising particles having a surface modified by hydrophilic molecules of polysaccharide type, e.g. by dextran molecules, which can be administered in vivo and wherein the particles have a long residence time in the organisms into which they are introduced.

The invention further aims at providing dispersions of magnetic particles of low hydrodynamic diameter which can be administered in vivo, in particular by injection, and which are suitable for making possible targeting to specific cells or organs for diagnostic purposes (composition of biospecific contrast agents for MRI, in particular) or for therapeutic purposes (targeted vectorization of active principles, in particular of medicaments, for example).

Thus, according to a first aspect, a subject matter of the present invention is an aqueous dispersion (hereinafter referred as "aminated ferrofluid"), which comprises particles (p) based on a magnetic iron oxide, and having dimensions of less than or equal to 20 nm, the surface of said particles being modified by the grafting of aminated groups R covalently bonded to the surface of the particles, wherein the isoelectric point of the particles with the surface so modified is greater than or equal to 10.

Within the sense of the present description, the term "aqueous dispersion of particles" is understood to mean a dispersion of particles in a medium of aqueous nature, such as water, an aqueous solution or alternatively a water/alcohol mixture.

The aminated ferrofluid of the invention generally exhibits similar magnetic and Theological characteristics to those of the aqueous ferrofluids of the prior art which are composed exclusively of particles based on iron oxide dispersed in an aqueous medium ("ungrafted" ferrofluids). Thus, the size and the morphology of the particles present are generally similar, as are the properties of the fluid under magnetic stress. However, unlike the ferrofluids of "ungrafted" type, the aminated ferrofluids of the invention additionally exhibit the advantage of having an isoelectric point of greater than 10,this isoelectric point generally being greater than or equal to 10.1 and advantageously greater than or equal to 10.2, indeed even greater than 10.3,this isoelectric point generally being less than or equal to 11 and generally less than or equal to 10.5. Thus, the particle size (p) with a modified surface present in a ferrofluid according to the invention are generally stable with regard to interparticle agglomeration in media having a pH of less than 8 and thus in particular in a neutral medium and especially at pH values of between 6 and 8,for example in a physiological medium, a range in which the "ungrafted" ferrofluids exhibit a marked tendency toward flocculation.

Preferably, an aminated ferrofluid according to the invention is provided in the form of an aqueous dispersion having a pH of less than or equal to 8. If appropriate, the aminated ferrofluid of the invention is generally provided in the form of a dispersion of particles having an average hydrodynamic diameter of less than or equal to 20 nm. In particular, when the particles (p) are of sufficiently small dimensions, typically between 5 and 7.5 nm, an aminated ferrofluid according to the invention with a pH of less than or equal to 8 is generally provided in the form of a stable colloidal dispersion of essentially separate particles.

Thus, generally, in an aminated ferrofluid according to the invention, at least 95% of the particles present, and preferably at least 98% of the particles present, are separate particles, i.e. not agglomerated with one or more other particles. In other words, an aminated ferrofluid according to the invention generally exhibits an extremely reduced level of interparticle aggregates. Thus, generally, in an aminated ferrofluid according to the invention, at most 5 (and preferably at most 2) solid components in suspension out of 100 are in the form of aggregates of particles. Generally, in an aminated ferrofluid according to the invention, interparticle aggregates with a size of greater than 30 nm are not observed.

The "average hydrodynamic diameter" to which reference is made here is the number-average hydrodynamic diameter as measured by photon correlation spectroscopy, for example with a device of Zetasizer type, such as in particular the Zetasizer 3000 HS sold by Malvern Instruments. This measurement method generally employs a capillary electrophoresis in combination with an analysis by Doppler effect laser interferometry. Photographs taken by transmission electron microscopy confirm in general this average hydrodynamic diameter, as do measurements carried out by X-ray diffraction. In general, the average hydrodynamic diameter of the grafted particles in the dispersions according to the invention is between 3 and 15 nm. It can be advantageous, in particular when use of the aminated ferrofluids of the invention in the preparation of a composition for in vivo administration, in particular by injection, is envisaged, for this hydrodynamic diameter to be less than 12 nm, advantageously less than 10 nm and more preferably less than 8 nm.

The particles (p) based on a magnetic iron oxide which are present in a composition according to the invention are generally particles composed, in all or part, of an iron oxide exhibiting magnetic properties and preferably ferrimagnetic properties. In these particles, the amount of magnetic iron oxide preferably represents at least 50% by weight, advantageously at least 60% by weight and more preferably still at least 90% by weight of the total weight of the inorganic compounds present in the particles, these particles preferably being composed essentially of one or more iron oxide(s) and the iron oxide being, in all cases, present at least at the surface of the particles (p). Preferably, the constituent magnetic iron oxide of the particles (p) of the aqueous dispersion of the invention is selected from ferrites of formula $MFe_2O_4$ (with M=CO, Ni, Cd, Mn, Zn or Mg), magnetite $Fe_3O_4$, maghemite ($\gamma$-$Fe_2O_3$) or the mixtures of these oxides. According to a preferred embodiment of the invention, the particles (p) are essentially composed of magnetite ($Fe_3O_4$) and/or of maghemite ($\gamma$-$Fe_2O_3$), and they are advantageously essentially composed of maghemite.

Thus, it is preferable for the particles (p) of the invention to be composed at least in a proportion of 95% by weight and advantageously at least in a proportion of 98% by weight of a ferrite, of a maghemite and/or of a magnetite.

Whatever their exact nature, it is preferable for the particles (p) to be particles of crystalline nature. Advantageously, the particles (p) are at least partly (and preferably essentially) monocrystals of iron oxide, advantageously monocrystals of magnetite or of maghemite.

Furthermore, in an aqueous dispersion of magnetic particles according to the invention, the particles (p) are grafted at the surface by aminated groups R, each of these groups R generally comprising a primary amine group —$NH_2$. Generally, these groups are generally provided in a protonated form. These aminated groups R, covalently bonded to the particle, are advantageously groups of formula —(A)—$NH_2$ in which the —A— group denotes a hydrocarbon chain comprising from 1 to 12 and preferably at most 8 carbon atoms, this chain optionally being interrupted by one or more —NH— groups, generally by 1 to 3 —NH— groups, if appropriate. Generally, in the group R, it is preferable for the —(A)— group to denote a linear chain. Furthermore, the —(A— group is advantageously a saturated hydrocarbon chain. According to an alternative form which can be envisaged, the —(A)— group can, however, comprise an aromatic ring.

In an especially advantageous way, the aminated groups R covalently which is bonded to the surface of the particles (p) of a dispersion according to the invention are selected from:

(i) the groups of formula —$(CH_2)n_1$—$NH_2$, where $n_1$=1, 2, 3, 4, 5, 6, 7 or 8,$n_1$ preferably being equal to 3, 4, 5 or 6 and advantageously equal to 3;

(ii) the groups of formula —$(CH_2)n_2$—NH—$(CH_2)$ $n_{2'}$—$NH_2$, where $n_2$ and $n_{2'}$ are identical or different and each denote 1, 2, 3, 4, 5 or 6,preferably 1, 2 or 3 and advantageously 2,it being understood that $(n_2+n_{2'})$ remains between 2 and 9;

(iii) the groups of formula —$(CH_2)n_3$—NH—$(CH_2)$ $n_{3'}$—NH—$(CH_2)n_{3''}$—$NH_2$, where $n_3$, $n_{3'}$ and $n_{3''}$ are identical or different and each denote 1, 2, 3 or 4,preferably 1, 2 or 3 and advantageously 2,it being understood that $(n_3+n_{3'}+n_{3''})$ remains between 3 and 12.

By way of example, the group R can be a group selected from the following groups:

—$(CH_2)_3$—$NH_2$;
—$(CH_2)_4$—$NH_2$;
—$(CH_2)_3$—NH—$(CH_2)_2$—$NH_2$.
—$(CH_2)_3$—NH—$(CH_2)_6$—$NH_2$.
—$(CH_2)_3$—NH—$CH(CH_3)$—$CH_2NH_2$.
—$(CH_2)_3$—NH—$(CH_2)_2$—NH—$(CH_2)_2$—$NH_2$;

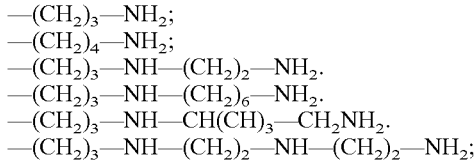

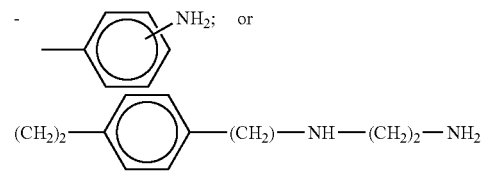

Whatever their exact nature, the aminated groups R are, characteristically, groups bonded to the particles (p) via a covalent bond. Generally, this covalent bond is provided via a silicon atom, according to the following schematic structure:

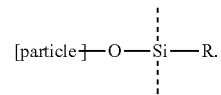

In other words, the groups R present at the surface of the particles (p) are generally obtained by reaction of a silane carrying the group R with the particles (p) based on magnetic iron oxide.

Generally, the average amount of groups R covalently bonded to the surface of the particles (p) is at least equal to 2 micromol per $m^2$ ($\mu mol/m^2$) and it is generally between 3 and 10 $\mu mol/m^2$, it being understood that it is preferable for it to remain greater than 4 $\mu mol/m^2$. Generally, this amount remains less than 8 $\mu mol/m^2$.

It should be stressed that a dispersion according to the invention is able to comprise a relatively large number of grafted particles. Thus, for a dispersion according to the invention, concentrations of particles (p) of greater than 30 grams of iron oxide per liter, indeed even of greater than 100 g/l and even, in some cases, of greater than 500 g/l can be envisaged. Thus, typically, an aminated ferrofluid according to the invention can comprise particles (p) in a proportion of 50 to 600 g of iron oxide. Given this possibility of employing such concentrations, the dispersions according to the invention may especially be of particular use as ferrofluids possessing superparamagnetic behavior. In this case, the particles (p) are preferably monocrystalline particles, preferably "monodomain" maghemite particles.

According to another aspect, the present invention relates to a process for the preparation of the aminated ferrofluids as described above.

This process is characterized in that it comprises the stages consisting in:

(A) providing an acidic aqueous dispersion of particles ($p_0$) based on a magnetic iron oxide with dimensions of less than 20 nm, said dispersion exhibiting, in an acidic medium, a colloidal stability at least within a pH range, this stability being such that, within said pH range, a dispersion of essentially separate particles having an average hydrodynamic diameter of less than 20 nm is observed, without having to keep stirring;

(B) bringing the acidic colloidal dispersion of stage (A) into contact with silanes of formula $R—SiX_1X_2X_3$, wherein:

R denotes an aminated group as defined above;

$X_1$, $X_2$ and $X_3$ are identical or different groups each denoting a group which can be hydrolyzed in an acidic medium, this contacting operation being carried out while maintaining the medium within the pH range where the colloidal stability of the dispersion is ensured, whereby silanols are formed by hydrolysis of the groups $X_1$, $X_2$ and $X_3$, in the medium of dispersion of the particles;

(C) adding, to the reaction medium, a water-soluble wetting agent with a boiling point greater than that of water and then heating the reaction medium to a temperature sufficient to remove the water but without removing the wetting agent, whereby the silanols are condensed at the surface of the particles while avoiding agglomeration of the particles (that remain dispersed in the wetting agent); and (D) recovering the particles obtained by stage (C) and dispersing them in an aqueous medium, whereby an aminated ferrofluid according to the invention is obtained.

In practice, it is observed that the hydrodynamic diameter of the particles present and the magnetic properties of the aminated ferrofluids obtained on conclusion of stage (D) are very similar, if not identical, to those of the acidic aqueous colloidal dispersion provided in stage (A). Thus, the magnetorheological properties of the dispersion obtained on conclusion of the preparation process of the invention are generally entirely determined by those of the acidic aqueous colloidal dispersions employed in stage (A).

The acidic aqueous colloidal dispersions employed in stage (A) are aqueous colloidal dispersions of particles based on iron oxide with a pH of generally less than 5, generally with a pH of between 2 and 4 and advantageously of less than 3. Preferably, the acidic aqueous colloidal dispersion of stage (A) is such that, in the pH range where the colloidal stability is ensured, the average hydrodynamic diameter of the particles which are observed in suspension is between 3 and 15 nm, it being possible for this diameter in some cases to be less than or equal to 12 nm, indeed even less than or equal to 10 nm or even, in some specific cases, less than or equal to 8 nm.

Furthermore, it is preferable, in the pH range where the colloidal stability is ensured, for less than 5% by number, advantageously less than 2% by number and preferably less than 1% by number of the solid entities which are observed in suspension to be agglomerates of several particles.

Generally, the acidic aqueous dispersion of stage (A) can thus be selected from the majority of the known stabilized aqueous "acidic ferrofluids" of the prior art exhibiting a suitable hydrodynamic diameter and a suitable colloidal stability. Thus, the acidic colloidal dispersion of stage (A) can advantageously be an acidic aqueous ferrofluid of particles of ferrites, of magnetite and/or of maghemite as obtained by employing the process described by Massart et al., for example in patent U.S. Pat. 4,329,241 or in *IEEE Trans. Magn.*, MAG-17(2), pp. 1247-1248 (1981).

Very advantageously, the acidic aqueous colloidal dispersion of stage (A) is a dispersion of maghemite particles prepared according to a process comprising the stages consisting in:

(a1) carrying out a coprecipitation of ferrous and ferric salts by adding a base, preferably in excess, to an aqueous solution comprising a mixture of iron(II) salts (and of iron(III) salts), so as to obtain a flocculate of magnetite particles;

(a2) after an optional separation of the flocculate, for example by magnetic separation (which generally proves to be advantageous), treating said flocculate of particles which is obtained with an acid selected from $HNO_3$, HCl or $CH_3COOH$, and advantageously with $HNO_3$, which makes it possible to acidify the surface of the particles and to carry out a surface oxidation of the particles by dissolution of ferrous ions;

(a3) adding, to the medium, a solution of a ferric salt and leaving to react, preferably while heating the medium (advantageously, the reaction is carried out by bringing the medium to boiling point, resulting in oxidation of the particles in the form of maghemite particles); and (a4) dispersing, in an aqueous medium, by addition of an acid selected from $HNO_3$ or $HClO_4$, the flocculate of maghemite particles which is obtained on conclusion of the preceding stage.

In this case, the conditions employed in stage (a1) of the above process are preferably as follows:

iron(II) salts used: ferrous chloride or ferrous sulfate, and advantageously ferrous chloride;

iron(III) salts used: ferric chloride or ferric nitrate, and advantageously ferric chloride;

Fe(III)/Fe(II) initial molar ratio: preferably of the order of 2;

base used for the coprecipitation: aqueous ammonia or sodium hydroxide. When sodium hydroxide is used, it is preferable for the coprecipitation medium to comprise sodium nitrate.

More generally, it should be noted that the treatment carried out in stages (B) to (D) of the process of the invention is most often a surface treatment which does not affect the internal physicochemical nature of the particles of the acidic aqueous colloidal dispersion of stage (A). Consequently, the chemical nature of the particles of the dispersion of stage (A) is generally the same as that of the particles (p) of the dispersion which it is desired to obtain on conclusion of stage (D).

According to an embodiment which can prove to be advantageous, the particles present in the acidic colloidal dispersions of stage (A) exhibit a BET specific surface of between 50 $m^2/g$ and 1000 $m^2/g$, this specific surface preferably being between 100 and 200 m²/g and advantageously of the order of 130 m²/g.

Stage (B) of the process of the invention consists in bringing the colloidal dispersion of stage (A) into contact with silanes exhibiting an aminated group R while keeping the particles in the dispersed state. This stage of bringing the silanes and the particles in the dispersed state into contact is generally carried out by addition of silanes to the suspension of particles provided during stage (A), and the medium obtained is generally left to react for a time of 2 to 15 hours, generally with stirring. The reaction is generally carried out at ambient temperature.

The silanes employed in stage (B) are preferably aminated trialkoxysilanes of formula R—Si(—OR')(—OR'')(—OR'''), wherein:
R is an aminated group as defined above; and
R', R'' and R''' are identical or different, and each denotes an alkyl group comprising from 1 to 5 carbon atoms, each of R', R'' and R''' preferably denoting a methyl group or an ethyl group, and advantageously a methyl group.

Thus, mention may in particular be made, as silanes which are particularly advantageous in stage (B), of:
γ-aminopropyltrimethoxysilane $(CH_3O)_3$—Si—$(CH_2)_3$—$NH_2$;
N-(β-aminoethyl)-γ-aminopropyltrimethoxysilane $(CH_3O)_3$—Si—$(CH_2)_3$—NH—$(CH_2)_2$—$NH_2$;
N'-(β-aminoethyl)-N-(β-aminoethyl)-γ-aminopropyl-trimethoxysilane $(CH_3O)_3$—Si—$(CH_2)_3$—NH—$(CH_2)_2$—NH—$(CH_2)_2$—$NH_2$.

Other silanes which can be contemplated in stage (B) are:
4-aminobutyltriethoxysilane,
N-(2-aminoethyl)-(3-aminoisobutyl)methyl-dimethoxysilane,
(aminoethylaminomethyl)phenethyltrimethoxy-silane,
N-(2-aminoethyl)-(3-aminopropyl)methyldimeth-oxysilane,
N-(2-aminoethyl)-3-aminopropyltrimethoxysilane,
N-(6-aminohexyl)aminopropyltrimethoxysilane,
m-aminophenyltrimethoxysilane,
p-aminophenyltrimethoxysilane,
3-aminopropylmethylbis(trimethylsiloxy)silane,
3-aminopropylmethyldiethoxysilane,
3-aminopropyltriethoxysilane,
3-aminopropyltrimethoxysilane.

Generally, whatever their nature, the silanes of stage (B) are introduced into the medium of stage (A) in the pure form, or in the form of a solution in an organic solvent, preferably, in that case in an alcohol, such as methanol or ethanol, and more advantageously in methanol. When the silanes are introduced in solution, the concentration of silane in the organic solvent is advantageously between 3 and 4% by weight.

The amount of silane introduced in stage (B) is generally adjusted in order to obtain the fullest possible coverage of the surface of the particles by the silane groups. To this end, it is generally preferable for the amount of silanes carrying the groups R which is introduced, with respect to the total available surface area developed by the particles (p) of the acidic colloidal dispersion of stage (A), to be at least equal to 2.5 μmol/m², and preferably at least equal to 10 μmol/m². The total available surface area developed by the particles (p) is calculated by multiplying the weight of the particles (in g) by the BET specific surface of these particles (in m²/g).

Characteristically, in the process of the invention, stage (B) is followed by a dehydration stage (C) carried out in the presence of a wetting agent. The purpose of this treatment is to carry out the dehydration while leaving particles in suspension in the wetting agent, whereby effective grafting of the silanol entities at the surface of the oxide particles is obtained while avoiding phenomena of interparticle aggregation which would be observed in the absence of wetting agent. This heat treatment stage can especially be of the type of that employed in the processes described in U.S. Pat. Nos. 4,524,088 or 4,695,393.

When the silanes of stage (B) are introduced in solution in an organic solvent, the wetting agent of stage (C) is preferably an agent which is soluble in the organic solvent which dissolves the silanes introduced in stage (B) and which has a boiling point greater than that of said organic solvent, and stage (C) generally comprises a stage of heating at a temperature sufficient to remove said organic solvent without removing the wetting agent. This removal of the solvent can be carried out in conjunction with the removal of the water, or else separately, and preferably prior to the removal of the water, if appropriate.

In all embodiments, a particularly advantageous wetting agent for carrying out stage (C) is glycerol.

Preferably, whatever the nature of the wetting agent, the heating of stage (C) is carried out under vacuum, which makes it possible in particular to operate at moderate temperature and to protect the grafting layer being synthesized. Thus, when the heating of stage (C) is carried out under vacuum, it proves to be particularly advantageous to carry out the dehydration of stage (C) at a temperature of less than or equal to 130° C. and preferably of less than 120° C. (typically of the order of 80 to 100° C.). Furthermore, if stage (C) comprises a stage of removal of an organic solvent, this stage is preferably carried out at a temperature which is as low as possible and advantageously at a temperature of less than or equal to 50° C.

Following stage (C), particles with a surface modified by the groups R are obtained within a medium which is essentially composed of the wetting agent (generally glycerol) and which also generally comprises unreacted silanes introduced during stage (B) and other possible by-products. Stage (D) of the process consists in recovering the particles from this medium and in then dispersing them in an aqueous medium.

Generally, stage (D) comprises a washing of the particles obtained on conclusion of stage (C), for example with acetone or with a water/acetone mixture. If appropriate, care is taken not to allow the particles to dry during the washing, which makes it possible in particular to avoid any phenomenon of interparticle agglomeration. The undried flocculate of particles which is obtained on conclusion of the washing is subsequently dispersed in an aqueous medium. The absence of drying during the washing makes possible optimum dispersion of the particles in an aqueous medium. The traces of washing solvent which are introduced into the aqueous medium (in particular the traces of acetone) can subsequently be removed, for example by entrainment under vacuum.

Advantageously, the dispersion of the particles which is produced during stage (D) is produced by placing the particles recovered on conclusion of stage (C) in water and by gradually reducing the pH of the medium by slow addition of an acid, such as nitric acid, hydrochloric acid or perchloric acid. Preferably, nitric acid is used. Furthermore, the gradual reduction in the pH is typically carried out in several stages, by decrementing the pH of the medium by one pH unit at each stage, preferably with moderate stirring. This stage of gradual reduction in the pH, referred to as "peptization by an acid", makes it possible to particularly well retain the grafting layer produced at the surface of the particles. When the abovementioned peptization technique is used, there is generally observed an optimum dispersion of the flocculate introduced in the form of separate particles when a pH of the order of 3 is reached. Once this dispersion is produced, the pH can be modified within the range of pH values of less than 8 without affecting the stability of the suspension obtained. In particular, the pH can be modified by addition of a base, for example sodium hydroxide or aqueous ammonia, in particular in order to obtain a stable aminated ferrofluid with a pH of between 6 and 8.

According to another aspect, a subject matter of the present invention relates to the uses which can be envisaged for the aminated ferrofluids defined above.

As stressed herein-above, the aminated ferrofluids of the invention exhibit similar characteristics to those of the conventional ferrofluids (reduced particle size in particular) but they further exhibit the advantage of being stable in a neutral medium, especially in the pH range between 6 and 8. Therefore, the aminated ferrofluids of the invention can generally be used in all the fields of application known for conventional ferrofluids but their stability in a neutral medium renders them suitable for other types of application.

Thus, in view of their stability, especially at pH values of the order of 7 and especially in a physiological medium, the aminated ferrofluids of the invention are actually of use in particular in the preparation of compositions of contrast agents for magnetic resonance imaging, very particularly in vivo. In such an application, the small size of the particles modified by the aminated groups R proves to be particularly suitable for good tissue diffusion. Furthermore, the inventors have moreover demonstrated that the surface modification by the aminated groups R carried out under the conditions of stages (A) and (B) also makes it possible to increase the stability of the starting acidic ferrofluids with regard to the presence of anions, such as chloride anions, for example, which are known to be capable of bringing about a loss of the stability of acidic ferrofluids, by canceling out the positive surface charges of the particles. This stabilization in the presence of anions proves to be particularly advantageous for in vivo applications, where the ferrofluid is often brought into contact with saline media.

Thus, generally, the aminated ferrofluids of the invention prove to be particularly advantageous in the preparation of compositions which can be administered orally or parenterally to man or animals, especially for therapeutic and/or diagnostic use, and in particular in the preparation of injectable compositions. The compositions for administration to man or animals obtained in this context, and in particular the injectable compositions of contrast agents for magnetic resonance imaging, constitute another subject matter of the invention.

The stability of the aminated ferrofluids of the invention over the entire pH range below 8 additionally makes it possible to envisage their use in other applications and in particular as magnetic filler in various magnetic compositions or materials, for example in polymer compositions or materials (where the particles of the ferrofluid can, for example, provide crosslinking between several molecules of polymers) or alternatively in materials of ceramic type. In this type of application, the aminated ferrofluids of the invention prove to be of particular use when the preparation of the compositions or materials employs an aqueous formulation. As regards this type of use, it should be remembered that the aminated ferrofluids of the invention comprise particles which are thermally stabilized. Especially, they are stable at a temperature of greater than 740 K and generally up to 1050 K. These particles can be used as magnetic fillers in the manufacture of magnetic materials, in particular ceramics, which can be used at temperatures of greater than 740 K, without loss of their magnetic properties.

Furthermore, as stressed herein-above, the aminated ferrofluids of the present invention comprise particles (p) to which are bonded aminated groups R that can react with chemical entities so as to modify the surface chemistry of the particles of the aminated ferrofluid. Surprisingly, the inventors have discovered that the stability of the particles of the aminated ferrofluids of the invention is such that the modification of the surface of the particles (p) by reaction of chemical entities with the groups R can be carried out without phenomena of interparticle aggregation being observed. Thus, the aminated ferrofluids of the invention can be used in the preparation of suspensions of essentially separate magnetic particles at the surface of which chemical entities are immobilized, where the immobilization of the chemical entities is achieved by establishing a bond, preferably a covalent bond, between said chemical entities and the aminated groups R present at the surface of the particles (p) present in the aminated ferrofluids.

In this context, a subject matter of the present invention is more specifically a process for the modification of the surface of the particles (p) of an aminated ferrofluid according to the invention, this process comprising a stage (G1) which consists in reacting said aminated ferrofluid with chemical entities E capable of forming a bond, preferably a covalent bond, with the aminated groups R present at the surface of the particles (p), this reaction being carried out under the conditions of stability of the aminated ferrofluid, namely, generally, at a pH of less than 8 and preferably at a lower pH, advantageously at a pH of less than or equal to 4 and preferably at a pH of less than or equal to 3.

The nature of the entities E employed in stage (G1) may vary to quite a large extent and it is within the competence of a person skilled in the art to determine the entities suitable for the surface modification of stage (G1) under the conditions of stability of the aminated ferrofluid used.

Generally, when the abovementioned stage (G1) is carried out, it is preferable for the aminated groups R present on the particles (p) of the aminated ferrofluid to exhibit —$NH_2$ groups. In this case, the chemical entities E used in stage (G1) preferably exhibit aldehyde —CHO, carboxyl —$COO^-$, acid anhydride, isothiocyanate —SCN, cyanate —CN or maleimide groups.

Advantageously, when the aminated groups R exhibit —$NH_2$ groups, the chemical entities E used in stage (G1) exhibit aldehyde groups. In this case, the reaction of stage (G1) generally consists in reacting the aminated ferrofluid with the chemical entities E carrying —CHO groups in the presence of a reducing agent, such as, for example, $NaBH_4$. The reaction which takes place at the surface of the particle can then be represented schematically by the following reaction sequence:

Stage 1:

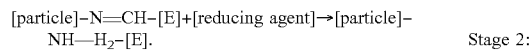
Stage 2:

According to a preferred embodiment, the entities E employed in stage (G1) are molecules of polysaccharides and advantageously dextran molecules, a portion of the —OH groups of which have been oxidized to give —CHO groups. If appropriate, the partial modification of the OH groups to give —CHO groups is carried out, for example, by a controlled oxidation by an oxidizing agent, such as sodium periodate $NaIO_4$, in particular according to the method described by Molteni in *Methods in Enzymology*, 112, 285-295 (1985).

However, it is possible to contemplate the use of other entities E in stage (G1). Thus, the entities E can, for example, be coloring agents, whereby the dispersions obtained can, for example, be used in the preparation of magnetic ink compositions. According to another alternative form which can be envisaged, the entities E can be compounds exhibiting an affinity for a given compound, in which case the dispersions obtained can be used to carry out a magnetic extraction of said compound (reaction between the particles and the compound, followed by extraction by a magnetic field of the particles which have reacted). This application can be taken advantage of in particular in processes for purification, for decontamination (in particular of waste water) or for extraction of advantageous compounds.

The aqueous dispersions of particles based on a magnetic iron oxide with a modified surface at the surface of which are immobilized chemical entities E, which can be obtained according to the abovementioned process for the modification of the aminated ferrofluids of the invention by carrying out stage (G1), constitute a specific subject matter of the present invention. These compositions will be denoted by the term of "modified aminated ferrofluid" in the continuation of the description.

In a "modified aminated ferrofluid" according to the invention, the particles present are generally well separated. Thus, generally, at least 90% by number and preferably at least 95% by number of the solid components present in a modified aminated ferrofluid according to the invention are separate particles comprising a single central core based on a magnetic iron oxide, this core having dimensions of less than 20 nm.

Generally, a modified aminated ferrofluid according to the invention exhibits a structure which is extremely similar to that of the starting aminated ferrofluid, with only a modification of the surface of the particles. In particular, it should be noted that stage (G1) does not modify the particles based on iron oxide themselves, which are generally identical to those present in the starting ferrofluid. Thus, in a modified aminated ferrofluid according to the invention, the particles based on iron oxide are preferably maghemite particles, preferably monocrystalline ("magnetic monodomain") maghemite particles, which advantageously have a size of less than 20 nm and generally of between 3 and 15 nm.

The modified aminated ferrofluids where the entities E are polysaccharides, a portion of the —OH groups of which have been oxidized to give —CHO groups, constitute particularly advantageous modified aminated ferrofluids according to the invention. In this context, the modified aminated ferrofluids where the entities E are dextran molecules, a portion of the —OH groups of which have been oxidized to give —CHO groups, are very particularly advantageous.

The inventors have demonstrated that these specific modified aminated ferrofluids exhibit the advantages of the ferrofluids of "USPIO" (or "MION") type currently known (namely, a small particle size and coverage of the particles by polysaccharides) with, moreover, an additional advantage, namely effective immobilization of the molecules of polysaccharides at the surface of the particles. This effective immobilization, which is not provided in the ferrofluids currently known, makes it possible (i) to increase the plasma half life of the particles when they are administered in vivo (the half life of the particles, which reflects the time during which the particles are not recognized and removed by the immune system, is dependent in particular on the stability of the immobilization of the polysaccharides of dextran type at the surface of the particles) and (ii) to allow grafting of chemical entities to the covering layer of polysaccharides without resulting in phenomena of depletion of the polysaccharides or of interparticle agglomeration.

In the following description, the modified aminated ferrofluids where the entities E are polysaccharides, a portion of the —OH groups of which have been oxidized to give —CHO groups, which constitute a particularly advantageous alternative to the ferrofluids of "USPIO" type, will be denoted by the term of "VUSPIO ferrofluid" ("Versatile Ultrasmall SuperParamagnetic Iron Oxides"). These "VUSPIO" ferrofluids constitute a specific subject matter of the present invention.

A "VUSPIO" ferrofluid is generally provided in the form of an aqueous dispersion of particles based on a magnetic iron oxide with dimensions generally of less than 20 nm and typically of between 3 and 15 nm, at the surface of which are immobilized, by covalent bonding, molecules of polysaccharides bonded to the surface via —NH—$CH_2$— covalent bonds. The "VUSPIO" ferrofluids where the molecules of polysaccharides are dextran molecules are particularly advantageous.

Generally, in a "VUSPIO" ferrofluid, the average hydrodynamic diameter of the particles with a surface modified by the molecules of polysaccharides is less than 50 nm and it is generally less than or equal to 40 nm, even less than or equal to 30 nm, in particular when the molecules of polysaccharides are dextran molecules.

Furthermore, in a "VUSPIO" ferrofluid, it is possible to obtain a very low and extremely reduced degree of particle agglomeration. Thus, a "VUSPIO" ferrofluid can, for example, be such that, as solid components in suspension, it essentially (namely, for at least 90%, preferably for at least 95% and advantageously for at least 98%) comprises separate particles comprising a single central core, based on an iron oxide, having dimensions of less than 20 nm, this core being surrounded by a layer comprising the covalently bonded molecules of polysaccharides. This structure can in particular be observed when the polysaccharides are dextran molecules.

More generally, a "VUSPIO" ferrofluid can comprise particles comprising a "core" composed of 1 to 250 inorganic particles "trapped" in a matrix of polysaccharides. The number of particles trapped in the matrix of polysaccharides can, however, be adjusted to quite a large extent. According to a particularly advantageous form, this number of cores is less than 100, preferably less than 50 and advantageously less than 10. Particularly advantageously, this number is less than 5 and it is particularly advantageous for this number to be of the order of 1 to 3. The "VUSPIO" ferrofluids where the bulk of the particles are composed of a single core surrounded by a matrix of polysaccharides constitute a specific subject matter of the invention.

In a "VUSPIO" ferrofluid according to the invention, the iron oxide/polysaccharide ratio by weight is preferably between 10:90 and 90:10 and advantageously between 30:70 and 40:60, this ratio advantageously being of about 35:65.

Preferably, in a "VUSPIO" ferrofluid according to the invention, the particles based on magnetic iron oxide are composed essentially of maghemite ($\gamma$-$Fe_2O_3$). Advantageously, these particles are monocrystalline ("magnetic monodomain"). In this case in particular, the "VUSPIO" ferrofluids according to the invention prove to be of particular use in the preparation of compositions of contrast agents for magnetic resonance imaging and in particular in the preparation of compositions for in vivo administration, in particular by injection. The compositions of contrast agents for magnetic resonance imaging which comprise a "VUSPIO" ferrofluid constitute another specific subject matter of the present invention.

Furthermore, it should be noted that, in a "VUSPIO" ferrofluid, a portion of the —OH groups of the molecules of polysaccharides which are immobilized at the surface of the particles are oxidized in the form of —CHO groups. This is because, generally, only a portion of the —CHO groups of the oxidized polysaccharides used in stage (G1) for modification of an aminated ferrofluid according to the invention are involved in the reaction with the aminated groups R. The residual —CHO groups prove to be particularly advantageous insofar as they make it possible to immobilize chemical entities at the surface of the particles of the "VUSPIO" ferrofluids. More generally, whether or not such residual —CHO groups exist, the stability of the "VUSPIO" ferrofluids is generally such that it is possible to envisage the grafting of chemical entities at the surface of the particles of these specific ferrofluids without observing significant phenomena of interparticle agglomeration. In other words, a "VUSPIO" ferrofluid proves to be of use in the manufacture of dispersions of separate magnetic particles at the surface of which chemical entities F are immobilized, where the grafting of the chemical entities is carried out by establishing a bond, preferably a covalent bond, between said chemical entities F and the molecules of polysaccharides.

According to a last aspect, a subject matter of the present invention is this specific use of the "VUSPIO" ferrofluids and the compositions obtained by modification of the surface of the particles of these specific ferrofluids.

In particular, a subject matter of the invention is the use of the "VUSPIO" ferrofluids where the immobilized polysaccharides have a portion of their —OH groups oxidized in the form of —CHO groups in the manufacture of dispersions of separate magnetic particles at the surface of which chemical entities F are immobilized, where the immobilization of said entities F is carried out by establishing a covalent bond between the entities F and the —CHO groups present on the molecules of polysaccharides. Where appropriate, the entities F preferably exhibit one or more $NH_2$ groups.

More specifically, a subject matter of the invention is a process for the modification of the surface of the particles present in a "VUSPIO" ferrofluid comprising a stage (G2) which consists in reacting said "VUSPIO" ferrofluid with chemical entities F capable of forming a bond, preferably a covalent bond, with the molecules of polysaccharides. In this process, the "VUSPIO" ferrofluid used is preferably a ferrofluid where the immobilized polysaccharides have a portion of their —OH groups oxidized in the form of —CHO groups, the chemical entities F then generally having an $—NH_2$ group. If appropriate, stage (G2) generally consists in reacting the "VUSPIO" ferrofluid with the entities F and in then treating the medium obtained with a reducing agent, for example sodium borohydride.

On carrying out the abovementioned modification process, aqueous dispersions of particles based on a magnetic iron oxide are obtained, molecules of polysaccharides, advantageously dextran molecules, being immobilized by covalent bonding at the surface of these particles via covalent bonds of formula $—NH—CH_2—$, these molecules of polysaccharides being themselves bonded to chemical entities F, preferably also via covalent bonds. These specific aqueous suspensions will be denoted in the continuation of the description by the term of "functionalized VUSPIO ferrofluid".

The "functionalized VUSPIO ferrofluids" according to the invention can be used in numerous fields of application.

Thus, these ferrofluids can be used in particular in the preparation of compositions of contrast agents for medical imaging having an affinity for given cells, tissues or organs. In this context, the entities F are selected from entities exhibiting an affinity with regard to the cells, tissues or organs for which the specificity is desired. The compositions of contrast agents for medical imaging comprising a VUSPIO ferrofluid functionalized by such entities F constitute another specific subject matter of the invention.

The "functionalized VUSPIO" ferrofluids according to the invention can also be employed in the preparation of compositions for therapeutic use. These compositions for therapeutic use constitute another subject matter of the present invention. In this context, the entities F are (or comprise) therapeutic active principles, in particular pharmaceutical active principles, or else oligonucleotides. These entities can then be vectorized to specific cells or organs, the small size of the ferrofluid making it possible to cross the various physiological barriers.

Furthermore, the compositions for therapeutic use based on "functionalized VUSPIO" ferrofluids according to the invention are suitable for the delivery of the active principles, with monitoring of the distribution of the active principle, in particular by MRI. For applications in the administration of active principles in vivo with monitoring of the distribution, it proves to be particularly advantageous to use ferrofluids of "functionalized VUSPIO" type where the entities F employed comprise (i) therapeutic active principles and (ii) labels, such as fluorochrome entities. The magnetic nature of these particles allows them to be located roughly in the body, for example by MRI, and then they can be located more precisely using the labels of fluorochrome type, which, for example, color the tissues where the active principle is carried, making possible identification of said tissues.

Generally, the compositions for therapeutic use or for diagnostic use (contrast agents for medical imaging) comprising dispersions according to the invention exhibiting particles grafted by entities of diagnostic or therapeutic interest are generally provided in the form of compositions which can be administered orally or parenterally and in particular in the form of injectable compositions. In this context, the compositions according to the invention can comprise, in addition to the particles present in dispersion, one or more additives suitable for the administration envisaged and in particular a vehicle suitable for the method of administration chosen.

Various advantages and characteristics of the invention will emerge even more clearly in the light of the illustrative examples given below.

Example 1

Synthesis of Aqueous Dispersions of Nanometric Maghemite Particles with a Surface Modified by Coupling of Aminosilanes (Aminated Ferrofluids)

1.1. Synthesis of Aqueous Dispersions of Nanometric Maghemite Particles (Acidic Ferrofluids)
1.1.1. Dispersion (D1)
An aqueous dispersion (D1) of nanometric maghemite particles was prepared by carrying out the following stages:

Formation of magnetite particles: 31.41 g (i.e., 0.158 mol) of ferrous chloride were dissolved in 170 ml of 1.5M hydrochloric acid. This solution was introduced into a 5 l beaker containing 85.4 g (i.e., 0.316 mol) of ferric chloride dissolved in 3.5 l of water. Coprecipitation of iron salts was carried out by addition of 200 ml of a 2M aqueous ammonia solution at 25° C. with stirring, which resulted in the formation of a colloidal magnetite precipitate. The magnetite particles obtained were allowed to separate by settling on a magnetic plate and then the supernatant was removed.

Desorption of the $NH_4^+$ counterions and surface oxidation: the flocculate prepared in the preceding stage was treated for a period of time of 15 minutes with 200 ml of nitric acid with a concentration of 2M. This treatment with nitric acid was carried out both in order to acidify the surface of the particles by desorbing the (flocculating) $NH_4^+$ counterions and by replacing them with nitrate ions and in order to dissolve the ferrous ions by surface oxidation. The flocculate was subsequently separated by settling and the supernatant was again removed.

Oxidation of the core of the particles: 600 ml of an aqueous ferric nitrate solution with a concentration of 0.33M, brought beforehand to boiling point, were subsequently introduced. Reaction was allowed to take place for 30 minutes, then separation was carried out magnetically and the supernatant was removed. In this stage, the contribution of the $Fe^{3+}$ ions in solution brings about the oxidation of the Fe(II) of the particles, which results in the formation of a $\gamma$-$Fe_2O_3$ maghemite phase in the particles.

Peptization: The medium obtained was treated with 200 ml of nitric acid with a concentration of 2M. During this stage, the protons contributed by the acid are adsorbed at the surface of the oxide particles, whereby a surface charge is obtained which makes possible interparticle electrostatic repulsion.

The medium was subsequently subjected to magnetic separation, whereby a flocculate of maghemite particles was obtained and was washed three times with acetone. Care was taken, during these washing operations, not to allow the flocculate to dry, in order to prevent the particles from agglomerating. The maghemite flocculate thus washed (and not dried) was subsequently placed in 500 ml of deionized water, whereby an aqueous dispersion of particles in the sol state was obtained. The residual acetone was removed by evaporation under vacuum at 40° C. The volume was subsequently brought to one liter by addition of 10 MΩ ultrapure water.

1.1.2. Dispersion (D2)

An aqueous dispersion (D2) of maghemite particles was produced by carrying out the following stages:

Formation of magnetite particles: 31.41 g (i.e., 0.158 mol) of ferrous chloride and 127.66 g of ferric nitrate were dissolved in a 5 liter beaker containing 2.5 liters of a 1M aqueous sodium nitrate solution. Coprecipitation of the iron salts was subsequently carried out by addition of a sodium hydroxide solution with a concentration of 5M until a pH of 13.2 was obtained, which resulted in the formation of a colloidal magnetite precipitate which was kept stirred for 15 minutes. The magnetite particles obtained were left to separate by settling on a magnetic plate and the supernatant was removed. The flocculate obtained was subsequently washed with two times 2 liters of water.

Desorption of the $NH_4^+$ counterions and surface oxidation: the flocculate from the preceding stage was treated for a period of time of 15 minutes with 400 ml of nitric acid with a concentration of 2M.

Oxidation of the core of the particles: the medium obtained was brought to boiling point and 600 ml of an aqueous ferric nitrate solution with a concentration of 0.33M were introduced therein. Reaction was allowed to take place for 30 minutes, which resulted in the formation of a $\gamma Fe_2O_3$ maghemite phase in the particles, and then the particles were magnetically separated and the supernatant was removed.

Peptization: the medium obtained was treated with 200 ml of 2M nitric acid, so as to obtain a surface charge which brings about interparticle electrostatic repulsion.

The medium was subjected to magnetic separation, whereby a flocculate of maghemite particles was obtained and was washed three times with acetone, care being taken not to allow the flocculate to dry. The maghemite flocculate, thus washed (and undried), was subsequently placed in 500 ml of deionized water, whereby an aqueous dispersion of particles in the sol state was obtained. The residual acetone was removed by evaporation under vacuum at 40° C. The volume was subsequently brought to 1 liter by addition of 10 MΩ ultra pure water.

1.1.3. Dispersion (D3)

A dispersion (D3) of maghemite particles was prepared by carrying out the following stages:

Formation of magnetite particles: 31.41 g (i.e., 0.158 mol) of ferrous chloride and 127.66 g of ferric nitrate were dissolved in a 5 liter beaker containing 2.5 liters of a 3M aqueous sodium nitrate solution. Coprecipitation of the iron salts was subsequently carried out by addition of a sodium hydroxide solution with a concentration of 5M until a pH of 13.2 was obtained, which resulted in the formation of a colloidal magnetite precipitate which was kept stirred for 15 minutes. The magnetite particles obtained were left to separate by settling on a magnetic plate and the supernatant was removed. The flocculate obtained was subsequently washed with two times 2 liters of water.

Desorption of the $NH_4^+$ counterions and surface oxidation: the flocculate produced in the preceding stage was treated for a period of time of 15 minutes with 400 ml of nitric acid with a concentration of 2M.

Oxidation of the core of the particles: the medium obtained was brought to boiling point and 600 ml of an aqueous ferric nitrate solution with a concentration of 0.33M were introduced therein. Reaction was allowed to take place for 30 minutes, which resulted in the formation of a $\gamma Fe_2O_3$ maghemite phase in the particles, and then the particles obtained were magnetically separated and the supernatant was removed.

Peptization: the sol obtained was treated with 200 ml of 2M nitric acid. During this stage, the protons contributed by the acid adsorb at the surface of the oxide particles, whereby a surface charge is obtained which makes possible repulsion.

The medium obtained was subsequently subjected to magnetic separation, whereby a flocculate of maghemite particles was obtained and was washed three times with acetone, care being taken not to allow the flocculate to dry. The maghemite flocculate, thus washed (and undried), was subsequently placed in 500 ml of deionized water, whereby an aqueous dispersion of particles in the sol state was obtained. The residual acetone was removed by evaporation under vacuum at 40° C. The volume was subsequently brought to 1 liter by addition of 10 MΩ ultra pure water.

The physicochemical characteristics of the dispersions (D1) to (D3) are combined in table 1 below.

TABLE 1

Physicochemical characteristics of the dispersions (D1) to (D3)

| Dispersion | (D1) | (D2) | (D3) |
|---|---|---|---|
| pH | 2.5 | 2.5 | 2.5 |
| Maghemite concentration | 28 g/l | 28 g/l | 28 g/l |
| Isoelectric point | 7.3 | 7.3 | 7.3 |
| Number-average hydrodynamic diameter, TEM[1] | 7.8 nm | 4.0 nm | 1.5 nm |
| Number-average hydrodynamic diameter, PCS[2] | 8.5 nm | 2.9 nm | 2 nm |

[1]as estimated by transmission electronic microscopy
[2]average hydrodynamic diameter as measured by photon correlation spectroscopy 1.2 Modification of the Surface of the Maghemite Particles in the Acidic Ferrofluids Synthesized in Examples 1.1.1 to 1.1.3

Various dispersions of maghemite particles with a modified surface (aminated ferrofluids) recorded as (D1a), (D1b), (D1c), (D2a) and (D3a) were prepared from the stabilized acidic ferrofluids (D1), (D2) and (D3) synthesized in the preceding stages. Surface modification was carried out with various aminosilane compounds by employing the following general protocol:

Coupling Reaction:

A volume of 200 ml of the ferrofluid under consideration ((D1), (D2) or (D3), depending on the circumstances), with an $Fe^{3+}$ concentration of 0.35M, was stirred magnetically at a rate of 300 revolutions per minute. 100 ml of industrial grade methanol were added with stirring to this ferrofluid. A solution in 100 ml of methanol of an amount of aminosilane compound corresponding to 148.3 micromol of silane per $m^2$ of surface area developed by the particles of the ferrofluid under consideration, namely 0.1 mol for the ferrofluid (D1), 0.2 mol for (D2) and 0.5 mol for (D3), was subsequently added to the mixture, kept stirred. The reaction was allowed to continue for 12 hours.

Heat Treatment (Dehydration)

Subsequent to the preceding stage, 200 ml of glycerol were added and the medium was homogenized for a few minutes by stirring at 500 revolutions per minute. The methanol and the water were subsequently extracted using a rotary evaporator (extraction under low vacuum for 1 hour, at 40° C. for the methanol and then at 80° C. for the water).

The medium obtained was subsequently subjected to a heat treatment at 100° C. under ultrahigh vacuum (vane pump) for 2 hours. The medium was subsequently allowed to cool to ambient temperature.

Extraction, Washing

The mixture obtained on conclusion of the heat treatment (modified maghemite particles in a medium composed essentially of glycerol, additionally comprising unreacted silane) was introduced into a beaker into which were successively poured 100 ml of ethanol and then 200 ml of acetone with slow stirring (100 revolutions per minute), so as to bring about flocculation of the modified maghemite particles and precipitation of the excess oligomerized silane.

The particles were separated on a magnetic plate and the supernatant, comprising the oligomerized silane, was removed. The flocculate of particles which was obtained was washed with three times 400 ml of an acetone/ultrapure water (70:30 v/v) mixture, so as to remove the residual silane oligomers and the residual glycerol. Here again, the washing operations were carried out so as not to allow the flocculate to dry.

Peptization

After the final washing of the preceding stage, 400 ml of ultrapure water were added to the flocculate obtained. The pH was then measured as equal to 10.4, testifying to the presence of amine functional groups at the surface of the maghemite and to the saturation of this surface by the amine functional groups.

1M nitric acid was then added to the medium, dropwise and with vigorous stirring (of the order of 700 revolutions per minute), so as to gradually reduce the pH, step by step, by approximately one pH unit at each stage. This acidification makes it possible in particular to retain the adhesion of the aminated polysiloxane film which was formed in the preceding stages on the surface of the particles.

When a pH of 6 was reached, the maghemite particles began to disperse. The pH of the medium was adjusted to 3 and the medium was left stirring for one day. The pH was subsequently again readjusted to 3.

Under these conditions, the following 5 dispersions (aminated ferrofluids) were prepared:

| | Starting acidic ferrofluid | | | | |
|---|---|---|---|---|---|
| | (D1) | (D1) | (D1) | (D2) | (D3) |
| Aminosilane compound used for the modification | APS[3] | EDPS[4] | DTPS[5] | APS | APS |
| Aminated ferrofluid obtained | (D1a) | (D1b) | (D1c) | (D2a) | (D3a) |

[3]APS: γ-aminopropyltrimethoxysilane
[4]EDPS: N-β-(aminoethyl)-γ-aminopropyltrimethoxysilane
[5]DTPS: N-β-(aminoethyl)-N'-β-(aminoethyl)-γ-aminopropyltrimethoxysilane 1.3. Properties of the Dispersions of Modified Maghemite Particles (Aminated Ferrofluids) Obtained The characteristics of the five aminated ferrofluids obtained are combined in table 2 below.

TABLE 2

Properties of the aminated ferrofluids obtained

| | Aminated ferrofluid | | | | |
|---|---|---|---|---|---|
| | (D1a) | (D1b) | (D1c) | (D2a) | (D3a) |
| pH | 3 | 3 | 3 | 3 | 3 |
| Fe concentration | 0.35M | 0.35M | 0.35M | 0.35M | 0.35M |
| Isoelectric point | 10.4[6] | 10.2 | 10.1 | 10.4 | 10.4 |
| Number-average hydrodynamic diameter, PCS | 15.2 nm | 7.7 nm | 15.5 nm | 6.0 nm | 5.7 nm |

[6]By way of comparison, a dispersion was prepared by modifying the dispersion D1 with APS under the conditions of the general protocol described above but without carrying out the second stage of heat treatment. The isoelectric point of the composition was then measured as equal to 8.3.

Example 2

Stability with Regard to Flocculation in Presence of Chloride Ions

In order to illustrate the increased stability of the aminated ferrofluids of the invention in comparison with the acidic ferrofluids as regards flocculation, a comparative test was carried out which consists in introducing chloride ions at increasing concentrations in the two types of ferrofluids.

The flocculation limiting concentration observed at pH =3 for the dispersions (D1), (D1a), (D1b) and (D1c) of example 1 is shown in table 3 below. The flocculation limiting concentration is the minimum concentration of chloride ions in the dispersion, at the pH under consideration, from which flocculation is observed to begin, flocculation being an increase in the turbidity due to the formation and to the increase in the size of the flocculates in the medium. The limiting concentration corresponds to the concentration at which an increase in the optical density, measured at a wavelength of 800 nm, is observed.

TABLE 3

| Flocculation limiting concentration during the addition of chloride ions | | | | |
|---|---|---|---|---|
| Dispersion | (D1) | (D1$_a$) | (D1$_b$) | (D1$_c$) |
| Flocculation limiting concentration (Cl⁻)(*) | 0.05 mol/l | 0.14 mol/l | 0.17 mol/l | 0.21 mol/l |

It is seen, in the light of the above data, that the surface modification makes it possible to multiply by at least two the limiting concentration for flocculation in the presence of chloride ions.

Example 3

Grafting of Dextran Molecules (Synthesis of Modified Aminated Ferrofluids of "VUSPIO" Type Dextran molecules were grafted onto the particles of the aminated ferrofluids of example 1.2. Four different categories of dextran were tested (Dextran T5: $\overline{M}_w$=5000; Dextran T15: $\overline{M}_w$=15000; Dextran T40: $\overline{M}w$=40000 and Dextran T70: $\overline{M}_w$=70000).

The grafting was carried out according to the following protocol:

Activation of The Dextran:

A solution of 10 g of dextran in 200 ml of ultrapure water was prepared. 10 ml of a 2.06 mol.l⁻¹ aqueous NaIO$_4$ solution were added to this medium and the mixture was left stirring for 12 h. On conclusion of this oxidation stage, the periodic salts obtained were removed from the medium. To do this, the solution obtained, which is pale yellow, was poured into a cellulose dialysis tube (cutoff threshold of 12 400 g/mol⁻¹, Aldrich). Dialysis was carried out in a 5 l beaker containing ultrapure water. The water was replaced 5 times every 2 hours. The activated dextran solution obtained was stored at 4° C. The presence of aldehydes was confirmed by the Fehling test.

Grafting of the Activated Dextran to the Particles of an Aminated Ferrofluid

A volume of 200 ml of the 10 g/l activated dextran solution obtained above was poured into 20 ml of a ferrofluid as obtained in example 1.2. The mixture produced was left stirring for 24 h and then 10 ml of a 0.206 mol.l⁻¹ sodium borohydride solution were added. The medium obtained was left stirring at pH=9 for 4 h.

In all cases, a stable sol was obtained.

Purification of the Sol Obtained by Tangential Ultrafiltration:

An ultrafiltration system composed of a peristaltic pump (Millipore N80EL005), of silicone piping and of a cartridge (Prep/Scale™-TFF) including a poly(ether sulfone) membrane with a cutoff threshold of 100 kD was used.

The sol was placed in the retentate tank. After passage of the sol in the membrane, 1 l of water was poured into the tank in order to carry out the washing. The sol was washed and neutralized against 3 l of ultrapure water. The purified sol which was obtained is more dilute than the starting sol as the dead volume of the system is approximately 100 ml. A portion of the product remains clogged inside the membrane. However, this product is discharged after washing for several hours. The dispersion of particles was concentrated, by evaporation, to an $Fe^{3+}$ concentration of 0.08M.

The results obtained by grafting various dextrans to the aminated ferrofluids (D1a), (D2a) and (D3a) of example 1.2 are combined in the table below. The various modified aminated ferrofluids obtained are labeled (G1) to (G9).

TABLE 4

| Aminated ferrofluids modified by grafting dextrans | | | |
|---|---|---|---|
| Modified ferrofluid produced | Starting aminated ferrofluid | Dextran used for the grafting | Number-average hydrodynamic diameter (PCS) of the particles of the modified ferrofluid produced |
| (G1) | (D1a) | T70 | 59.6 nm |
| (G2) | (D1b) | T70 | 130 nm |
| (G3) | (D1c) | T70 | 130 nm |
| (G4) | (D1a) | T40 | 53.7 nm |
| (G5) | (D1a) | T15 | 132.8 nm |
| (G6) | (D2a) | T40 | 70.8 nm |
| (G7) | (D2a) | T15 | 46.7 nm |
| (G8) | (D2a) | T5 | 44.9 nm |
| (G9) | (D3a) | T40 | 56.5 nm |
| (G10) | (D3a) | T15 | 34.0 nm |
| (G11) | (D3a) | T5 | 32.2 nm |

Example 4

Synthesis of Functionalized "VUSPIO" Ferrofluids 4.1. Grafting of an Aminotelechelic (Diamino) Poly(Ethylene Oxide) to the Particles of the Modified Ferrofluids of Example 3.

Molecules of poly(ethylene oxide)-diamine were grafted to the particles of the modified aminated ferrofluids (G1) to (G3) of example 3.

The grafting was carried out according to the following protocol:

A solution of 20.5 g of POE-diamine ($M_w$=2000 g/mol) in 100 ml of water was added to a volume of 200 ml of the ferrofluid under consideration ((G1), (G2) or (G3), depending on the circumstances). 100 ml of an aqueous sodium borohydride solution with a concentration of 0.206 mol/l were subsequently added to the medium. Reaction was allowed to take place at pH 9 for 4 hours and with stirring, and the excess POE-diamine was subsequently removed under tangential ultrafiltration against 5 l of ultrapure water. The dispersion of borohydride and of borate obtained was concentrated by evaporation of the water until an Fe 3+concentration of 0.08M was obtained.

The results obtained in the three cases are given in table 5 below.

TABLE 5

Ferrofluids modified by grafting POE-diamine

| Starting ferrofluids | Number-average hydrodynamic diameter (PCS) of the particles of the ferrofluid produced |
|---|---|
| (G1) | 59.6 nm |
| (G2) | 53.7 nm |
| (G3) | 132.8 nm |

4.2. Grafting of a Monoamino Poly(ethylene Oxide) to the Particles of Modified Ferrofluids of Example 3

A grafting similar to that of example 4 was carried out using the aminated ferrofluids (G4), (G6) and (G9) of example 3, the procedure of example 4 being employed to do this, apart from the fact that a POE-monoamine ($M_w$=2000 g/mol) was used. Furthermore, the amount of POE was divided by two with respect to example 4. Thus, the POE solution added comprises 10.25 g of POE-monoamine in 100 ml of water.

The results obtained by the grafting of the aminated ferrofluids D1a, D2a and D3a of example 1.2 are combined in table 6 below.

TABLE 6

Ferrofluids modified by grafting with POE-monoamine

| Starting aminated ferrofluid | Number-average hydrodynamic diameter (PCS) of the particles of the modified ferrofluid produced |
|---|---|
| (G4) | 74.5 nm |
| (G6) | 62.1 nm |
| (G9) | 65.6 nm |

4.3. Grafting of the Particles of the Modified Ferrofluids of Example 3 with Fluorescent Entities 100 ml of the modified ferrofluids of example 3, with an $Fe^{3+}$ concentration of 0.08M, buffered with a phosphate buffer (pH 7.4; 0.01M), were allowed to react for 24 hours, with the exclusion of light, with $10^{-3}$ mol of Rhodamine B (Rh B) or Lucifer Yellow (LY) in the form of its dilithium salt. Reduction with borohydride was subsequently carried out under the conditions of example 3. These aminated entities react directly with the aldehyde functional groups of the oxidized dextrans. Subsequent to this reaction, the excess fluorescent entities (fluorochromes) were removed by liquid-liquid (water/chloroform) extraction until the organic phase became colorless. The traces of chloroform were subsequently removed on a rotary evaporator.

4.4 Grafting of the Particles of the Modified Ferrofluid of Example 4.1 with Fluorescent Entities The coupling reaction was carried out on 100 ml of ferrofluid according to example 4.1, with an $Fe^{3+}$ concentration of 0.08M, buffered with a carbonate/sodium bicarbonate buffer (pH 9, 0.01M), with $10^{-3}$ mol of TRITC (tetramethylrhodamine isothiocyanate derivative) or of 5-FAM, SE (the succinimidyl ester of 5-carboxyfluorescein). The 5-FAM, SE was dissolved beforehand in 3 ml of DMF. The excess fluorescent entities were removed by liquid-liquid (water/chloroform) extraction until the organic phase became colorless. The traces of chloroform were removed on a rotary evaporator.

4.5: Grafting of the Particles of the Modified Ferrofluids of Example 6 with Fluorescent Entities The procedure used is identical to that of example 4.4, except that the POE-diamine is replaced by a mixture of POE-monoamine and POE-diamine in the proportions 2:1.

4.6: Grafting of Doxorubicin to the Particles of the Ferrofluids of Examples 4.1 and 4.2

$2.22 \times 10^{-4}$ mol of doxorubicin (number of moles equivalent to 1/30th of moles of glucoside residues) was added to the dispersion of nanometric particles prepared in example 3 before the reduction with borohydride. The procedure described in example 3 is subsequently followed. The particles treated with doxorubicin are then subjected to the same treatment as those resulting from example 4.1 or 4.2.

4.7: Grafting of Folic Acid to the Particles of the Ferrofluids of Example 3

4.7.1 Esterification of Folic Acid with N-hydroxysuccinimide (NHS):

5 g of folic acid were dissolved in 100 ml of DMSO. 2.5 ml of triethylamine, 2.6 g of NHS and 4.7 g of carbodiimide were added to this mixture. Reaction was allowed to take place overnight at ambient temperature. The coproduct of the reaction, dicyclohexylurea, was extracted by filtration. The solution of folic acid coupled to NHS was concentrated on an evaporator under reduced pressure. The product was then precipitated from diethyl ether.

4.7.2 Combination of POE-diamine with Folic Acid Coupled to NHS:

15 g of POE-diamine ($M_w$=2000 g/mol) were dissolved in 100 ml of a carbonate/bicarbonate buffer solution at pH 10.5. 4.5 g of the product (folic acid-NHS) obtained on conclusion of stage 4.7.1 were dissolved in the minimum amount of DMSO (10 ml). This solution was then run dropwise into the solution containing the POE-diamine and the reaction was allowed to take place for 12 h. The product was then dialyzed against ultrapure water for 12 h in a dialysis tube with a cutoff threshold of 1 kD while regularly changing the water.

4.7.3 Grafting of the Combined Product from Stage 4.7.2 to the Particles of Example 3:

The procedure is identical to that of example 4.5, the POE-monoamine being replaced by the POE-folic acid combined product from stage 4.7.2.

The invention claimed is:

1. An aqueous dispersion comprising particles (p) based on a magnetic iron oxide,
   said particles having dimensions of less than or equal to 20 nm, and
   a surface of said particles being modified by a grafting of aminated groups (R) covalently bonded to the surface of the particles,
   wherein, the aminated groups (R) are selected from the group consisting of:
   —$(CH_2)_3$—$NH_2$;
   —$(CH_2)_4$—$NH_2$;
   —$(CH_2)_3$—NH—$(CH_2)_2$—$NH_2$;
   —$(CH_2)_3$—NH—$(CH_2)_6$—$NH_2$;

—(CH$_2$)$_3$—NH—CH(CH)$_3$CH$_2$—NH$_2$;
—(CH$_2$)$_3$—NH—(CH$_2$)$_2$—NH—(CH$_2$)$_2$—NH$_2$;

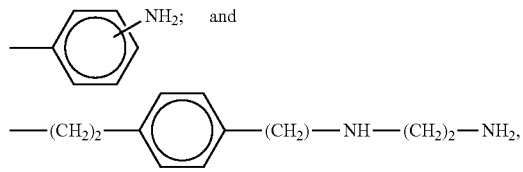

and
the isoelectric point of the particles with the surface so modified is greater than or equal to 10.

2. The aqueous dispersion of claim 1, wherein said dispersion has a pH of less than or equal to 8 and said dispersion of particles has an average hydrodynamic diameter of at most 20 nm.

3. The dispersion of claim 2, wherein the average hydrodynamic diameter of the particles (p) is between 3 and 15 nm.

4. The dispersion of claim 1, wherein the particles (p) consist essentially of maghemite (γ-Fe$_2$O$_3$), or monocrystalline maghemite.

5. The dispersion of claim 1, wherein the aminated groups (R) are bonded to the surface of the particles (p) via a bond:

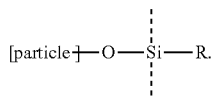

6. A process for the preparation of the dispersion of claim 1, comprising the stages of:
(A) providing an acidic aqueous dispersion of particles (p$_0$) based on a magnetic iron oxide with dimensions of less than 20 nm, said dispersion exhibiting, in an acidic medium, a colloidal stability at least within a pH range, this stability being such that, within said pH range, a dispersion of essentially separate particles having an average hydrodynamic diameter of less than 20 nm is observed, without having to constantly stir the dispersion;
(B) bringing the acidic colloidal dispersion of stage (A) into contact with silanes of formula R—SiX$_1$X$_2$X$_3$, wherein:
R denotes an aminated group;
X$_1$, X$_2$ and X$_3$ are identical or different groups, each denoting a group which can be hydrolyzed in an acidic medium,
this contacting operation being carried out while maintaining the medium within the pH range where the colloidal stability of the dispersion is ensured;
(C) adding to the reaction medium a water-soluble wetting agent with a boiling point greater than that of water and then heating the reaction medium to a temperature sufficient to remove the water but without removing the wetting agent; and
(D) recovering the particles obtained on conclusion of stage (C) and dispersing them in an aqueous medium.

7. The process of claim 6, wherein the acidic aqueous colloidal dispersion of stage (A) is such that, in the pH range where the colloidal stability is ensured, the average hydrodynamic diameter of the particles which are observed in suspension is between 3 and 15 nm.

8. The process of claim 6, wherein the acidic aqueous colloidal dispersion of stage (A) is such that, in the pH range where the colloidal stability is ensured, less than 5% by number of the solid entities which are observed in suspension are agglomerates of several particles.

9. The process of claim 6, wherein the silanes employed in stage (B) are aminated trialkoxysilanes of formula R—Si(OR')(OR'')(OR''') in which:
R is an aminated group; and
R', R'' and R''', which are identical or different, each denotes an alkyl group comprising from 1 to 5 carbon atoms.

10. The process of claim 9, wherein the silanes of stage (B) are selected from:
γ-aminopropyltrimethoxysilane, of formula:

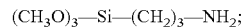

N-(β-aminoethyl)-γ-aminopropyltrimethoxysilane, of formula:

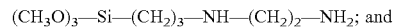

N'-(β-aminoethyl)-N-(β-aminoethyl)-γ-aminopropyltrimeth-oxysilane of formula:

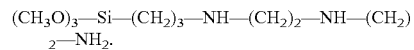

11. The process of claim 6, wherein:
the silanes of stage (B) are introduced in solution in an organic solvent;
the wetting agent of stage (C) is soluble in the organic solvent which dissolves the silanes introduced in stage (B) and has a boiling point greater than that of said organic solvent; and
stage (C) includes a heating step at a temperature sufficient to remove said organic solvent without removing the wetting agent.

12. The process as claimed in claim 6, wherein, in stage (C), the wetting agent is glycerol.

13. The process as claimed in claim 6, wherein the heating of stage (C) is carried out under vacuum.

14. The process as claimed in claim 13, wherein the dehydration of stage (C) is carried out at a temperature of less than or equal to 130° C.

15. The process as claimed in claim 6, wherein stage (D) comprises a washing of the particles obtained on conclusion of stage (C), carried out without allowing the particles to dry, followed by dispersion, in an aqueous medium, of the undried flocculate of particles which is obtained.

16. The process as claimed in claim 6, wherein the dispersion of the particles which is produced during stage (D) is produced by placing the particles recovered on conclusion of stage (C) in water and by gradually reducing the pH of the medium by slow addition of an acid.

17. A composition comprising the dispersion as claimed in claim 1, the composition formulated to be administered orally or parenterally to humans or animals.

18. A composition for administration to man or animals, comprising a dispersion as claimed in claim 1, and a physiologically acceptable vehicle.

19. A process for the modification of the surface of the particles (p) of a dispersion as claimed in claim 1, comprising a stage (G1) which consists of reacting said dispersion with chemical entities E capable of forming a bond with the aminated groups R present at the surface of the particles (p), at a pH of less than 8.

20. The process as claimed in claim 19, wherein the chemical entities E exhibit aldehyde groups, the aminated groups R exhibit —$NH_2$ groups and stage (G1) consists in reacting the dispersion with chemical entities E carrying —CHO groups in the presence of a reducing agent.

21. The process as claimed in claim 20, wherein the entities E are molecules of polysaccharides, a portion of the —OH groups of which have been oxidized to give —CHO groups.

22. The process as claimed in claim 21, wherein the entities E are dextran molecules, a portion of the —OH groups of which have been oxidized to give —CHO groups.

23. An aqueous dispersion of particles based on a magnetic iron oxide with a modified surface at the surface of which are immobilized chemical entities E, obtainable as claimed in the process of claim 19.

24. The dispersion as claimed in claim 23, wherein at least 90% by number of the solid components which it comprises are separate particles comprising a single central core based on a magnetic iron oxide having dimensions of less than 20 nm.

25. The dispersion as claimed in claim 23, in which the entities E are polysaccharides, for example dextran molecules, a portion of the —OH groups of which have been oxidized to give —CHO groups.

26. An aqueous dispersion of particles based on a magnetic iron oxide at the surface of which are immobilized, by covalent bonding, molecules of polysaccharides bonded to the surface via covalent bonds of formula —NH—$CH_2$—, said suspension being obtainable by the process of claim 21.

27. An aqueous dispersion of particles based on a magnetic iron oxide at the surface of which are immobilized, by covalent bonding, dextran molecules via covalent bonds —NH—$CH_2$—, this dispersion being obtainable by the process of claim 22.

28. The dispersion as claimed in claim 26, wherein the average hydrodynamic diameter of the particles with a surface modified by the molecules of polysaccharides is less than 50 nm.

29. The dispersion as claimed in claim 25, wherein at least 90% of the solid components in suspension are separate particles comprising a single central core, based on an iron oxide, having dimensions of less than 20 nm, this core being surrounded by a layer comprising the covalently bonded molecules of polysaccharides.

30. The dispersion as claimed in claim 25, wherein the particles based on magnetic iron oxide are essentially composed of maghemite ($\gamma$-$Fe_2O_3$).

31. The dispersion as claimed in claim 25, wherein a portion of the —OH groups of the molecules of polysaccharides immobilized at the surface of the particles are oxidized in the form of —CHO groups.

32. A composition of contrast agents for magnetic resonance imaging, comprising a dispersion as claimed in claim 25.

33. A process for the modification of the surface of the particles present in a dispersion as claimed claim 26, comprising a stage (G2) which consists in reacting said dispersion with chemical entities F capable of forming a bond with the molecules of polysaccharides.

34. The process as claimed in claim 33, where stage (G2) consists in reacting a dispersion with chemical entities F having an —$NH_2$ group and in treating the medium obtained with a reducing agent.

35. An aqueous dispersion of particles based on a magnetic iron oxide at the surface of which are immobilized, by covalent bonding, dextran molecules via covalent bonds of formula —NH—$CH_2$—, these dextran molecules being themselves bonded to chemical entities F, this dispersion being capable of being obtained as claimed in the process of claim 33.

36. A composition of a contrast agent for medical imaging having an affinity for given cells, tissues or organs, comprising a dispersion as claimed in claim 35, wherein the entities F are entities exhibiting an affinity with regard to said cells, said tissues or said organs.

37. A composition for therapeutic use, comprising a dispersion as claimed in claim 35, wherein the entities F are therapeutic active principles.

38. The composition as claimed in claim 36, provided in the form of an injectable composition.

39. An aqueous dispersion of particles, said particles comprising:
    a magnetic iron oxide core;
    amine groups (R) covalently bonded to a surface of the particles via a silane bond: (particle)—O—Si—R; and
    polysaccharide groups covalently bonded to the amine groups,
    wherein, the particles have an isoelectric point greater than or equal to 10.

40. The aqueous dispersion of particles according to claim 39, wherein the polysaccharide is dextran and the particles have a number-average hydrodynamic diameter (PCS) of less than 132.8 nm.

41. The composition of claim 1, wherein the composition is formulated to be an injectable composition of contrast agents for magnetic contrast imaging.

* * * * *